US011833265B2

(12) United States Patent
Lin et al.

(10) Patent No.: US 11,833,265 B2
(45) Date of Patent: Dec. 5, 2023

(54) MOBILE DEVICE FOR DISINFECTING AND STERILIZING WITH SPRAY AND ULTRAVIOLET LIGHT

(71) Applicant: TECO Electric & Machinery Co., Ltd., Taipei (TW)

(72) Inventors: Chia-Jen Lin, Taipei (TW); Shih-Chang Cheu, Taipei (TW)

(73) Assignee: TECO ELECTRIC & MACHINERY CO., LTD., Taipei (TW)

( * ) Notice: Subject to any disclaimer, the term of this patent is extended or adjusted under 35 U.S.C. 154(b) by 826 days.

(21) Appl. No.: 16/918,737

(22) Filed: Jul. 1, 2020

(65) Prior Publication Data

US 2021/0322611 A1 Oct. 21, 2021

(30) Foreign Application Priority Data

Apr. 20, 2020 (TW) .................................. 109113199

(51) Int. Cl.
*A61L 2/24* (2006.01)
*A61L 2/10* (2006.01)
*A61L 2/22* (2006.01)
*G05D 1/00* (2006.01)
*G05D 1/10* (2006.01)

(52) U.S. Cl.
CPC .................... *A61L 2/24* (2013.01); *A61L 2/10* (2013.01); *A61L 2/22* (2013.01); *G05D 1/0094* (2013.01); *G05D 1/101* (2013.01); *A61L 2202/11* (2013.01); *A61L 2202/14* (2013.01); *A61L 2202/15* (2013.01); *A61L 2202/16* (2013.01)

(58) Field of Classification Search
CPC ..... A61L 2/24; A61L 2/10; A61L 2/22; A61L 2202/11; A61L 2202/14; A61L 2202/15; A61L 2202/16; A61L 2202/25
See application file for complete search history.

(56) References Cited

U.S. PATENT DOCUMENTS

2016/0271803 A1\* 9/2016 Stewart ................ B25J 11/0085
2019/0321500 A1\* 10/2019 Anderson ................ A61L 2/10

\* cited by examiner

*Primary Examiner* — Lessanework Seifu
(74) *Attorney, Agent, or Firm* — Muncy, Geissler, Olds & Lowe, P.C.

(57) ABSTRACT

A mobile device includes a mobile platform, a spray generating assembly, an ultraviolet light-emitting module, a scanning module and a controlling module. The spray generating assembly is to generate a disinfecting and sterilizing spray for a spraying, disinfecting and sterilizing operation in the working area. The ultraviolet light-emitting module is configured to generate ultraviolet beams for performing a radiating, disinfecting and sterilizing operation onto a ground surface of the working area. The scanning module defined with an entire scan range is configured to generate a warning signal upon a human in the entire scan range. The controlling module, electrically connected with the scanning module and the spray generating assembly, is configured to control the spray generating assembly to stop generating the disinfecting and sterilizing sprays upon receiving the warning signal, so as to prevent the human from inhaling excessive sprays.

12 Claims, 10 Drawing Sheets

MOBILE DEVICE FOR DISINFECTING AND STERILIZING WITH SPRAY AND ULTRAVIOLET LIGHT

This application claims the benefit of Taiwan Patent Application Serial No. 109113199, filed Apr. 20, 2020, the subject matter of which is incorporated herein by reference.

BACKGROUND OF THE INVENTION

(1) Field of the Invention

The invention relates to a device, and more particularly to a mobile device for disinfecting and sterilizing with spray and ultraviolet light.

(2) Description of the Prior Art

Tuberculosis, atypical pneumonia (Severe acute respiratory syndrome, SARS), middle east respiratory syndrome (MERS) and other major infections are mainly transmitted through droplets or direct contact.

Wearing a medical mask can substantially avoid droplet infection. However, in addition to washing hands frequently or avoiding direct contact with eyes, mouth and nose, the more important attitude is to perform thorough environmental disinfecting and sterilizing, such that most contagious situations can be resolved.

Currently, disinfecting and sterilizing upon an infected zone are usually carried out by cleaning personnel wearing protective equipment. However, with human labors to perform disinfecting and sterilizing, a risk of infecting virus is always true. Thus, a room is always there for introducing improved environmental disinfecting and sterilizing.

SUMMARY OF THE INVENTION

In view that a risk of getting infection does always exist while the disinfecting and sterilizing is conducted by human, accordingly it is an object of the present invention to provide a mobile device for disinfecting and sterilizing with spray and ultraviolet light that can be used for resolving at least one of the aforesaid shortcomings in the art.

In this invention, the mobile device for disinfecting and sterilizing with spray and ultraviolet light, used for performing a spraying, disinfecting and sterilizing operation and a radiating, disinfecting and sterilizing operation in a working area, includes a mobile platform, a spray generating assembly, an ultraviolet light-emitting module, a scanning module and a controlling module.

The mobile platform is used for moving within the working area. The spray generating assembly, disposed on an external exposed surface of the mobile platform, is used for generating a disinfecting and sterilizing spray for performing the spraying, disinfecting and sterilizing operation in the working area. The ultraviolet light-emitting module, disposed at the mobile platform, is used for generating at least one ultraviolet beam to radiate a ground surface of the working area and thus to perform the radiating, disinfecting and sterilizing operation onto the ground surface. The scanning module, disposed at the mobile platform and defined with an entire scan range, is used for generating a warning signal upon when a human within the entire scan range is determined. The controlling module, electrically connected with the scanning module and the spray generating assembly, is used for controlling the spray generating assembly to stop generating the disinfecting and sterilizing spray upon when the warning signal is received, so as to prevent the human from inhaling excessively the disinfecting and sterilizing spray.

In one embodiment of the present invention, the spray generating assembly is disposed on a top surface of the external exposed surface of the mobile platform.

In one embodiment of the present invention, the spray generating assembly includes a spray head furnished with at least one spray nozzle for spraying out the disinfecting and sterilizing spray.

In one embodiment of the present invention, the spray generating assembly further includes a rotation member connected with the spray head, and is used for rotating in a rotation direction so as to have the at least one spray nozzle of the spray head to spray out the disinfecting and sterilizing spray in the rotation direction.

In one embodiment of the present invention, the spray generating assembly further includes a main body having an accommodation space for containing a disinfection liquid, the accommodation space is spatially connected with the at least one spray nozzle, and the disinfection liquid is used for forming the disinfecting and sterilizing spray.

In one embodiment of the present invention, the controlling module includes an ultraviolet control unit electrically connected with the ultraviolet light-emitting module and used for controlling the ultraviolet light-emitting module to stop generating the at least one ultraviolet beam upon when the warning signal is received.

In one embodiment of the present invention, the scanning module includes a first scan unit and a second scan unit. The first scan unit for scanning toward a first direction has a first partial scan range defined by two first scan boundaries. The second scan unit for scanning toward a second direction reverse to the first direction has a second partial scan range defined by two second scan boundaries. The two first scan boundaries are located within the second partial scan range, the two second scan boundaries are located within the first partial scan range, and the first partial scan range integrates the second partial scan range to form the entire scan range for covering surroundings of the mobile platform.

In one embodiment of the present invention, the mobile device for disinfecting and sterilizing with spray and ultraviolet light further includes a path-generating module. The path-generating module electrically connected with the controlling module is used for generating a patrol route with respect to the working area, and the controlling module is used for controlling the mobile platform in a patrol mode to move along the patrol route and further for controlling the spray generating assembly to generate the disinfecting and sterilizing spray.

In one embodiment of the present invention, the spray generating assembly is disposed on a lateral surface of the external exposed surface of the mobile platform.

In one embodiment of the present invention, the spray generating assembly includes a plurality of wheels for assisting the spray generating assembly to move with the mobile platform.

In one embodiment of the present invention, the mobile device for disinfecting and sterilizing with spray and ultraviolet light further includes an additional light-emitting module disposed at the spray generating assembly for generating a plurality of additional ultraviolet beams to perform an additional disinfecting and sterilizing operation in the working area.

In one embodiment of the present invention, the controlling module includes an additional control unit electrically connected with the additional light-emitting module for controlling the additional light-emitting module to stop generating the plurality of additional ultraviolet beams upon when the warning signal is received.

As stated, the mobile device for disinfecting and sterilizing with spray and ultraviolet light provided by this invention utilizes the mobile platform, the spray generating assembly and the ultraviolet light-emitting module to perform the spraying, disinfecting and sterilizing operation and the radiating, disinfecting and sterilizing operation in the working area, while in moving within the working area. Thereupon, aforesaid shortcomings related to human labors and environments can be substantially resolved. In addition, the spraying, disinfecting and sterilizing operation and the radiating, disinfecting and sterilizing operation are integrated to provide superior disinfection performance to any conventional spraying, disinfecting and sterilizing operation or any conventional radiating, disinfecting and sterilizing operation.

All these objects are achieved by the method and the mobile device for disinfecting and sterilizing with spray and ultraviolet light described below.

BRIEF DESCRIPTION OF THE DRAWINGS

The present invention will now be specified with reference to its preferred embodiment illustrated in the drawings, in which.

DESCRIPTION OF THE PREFERRED EMBODIMENT

The invention disclosed herein is directed to a mobile device for disinfecting and sterilizing with spray and ultraviolet light. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to unnecessarily obscure the present invention.

Figure 1:
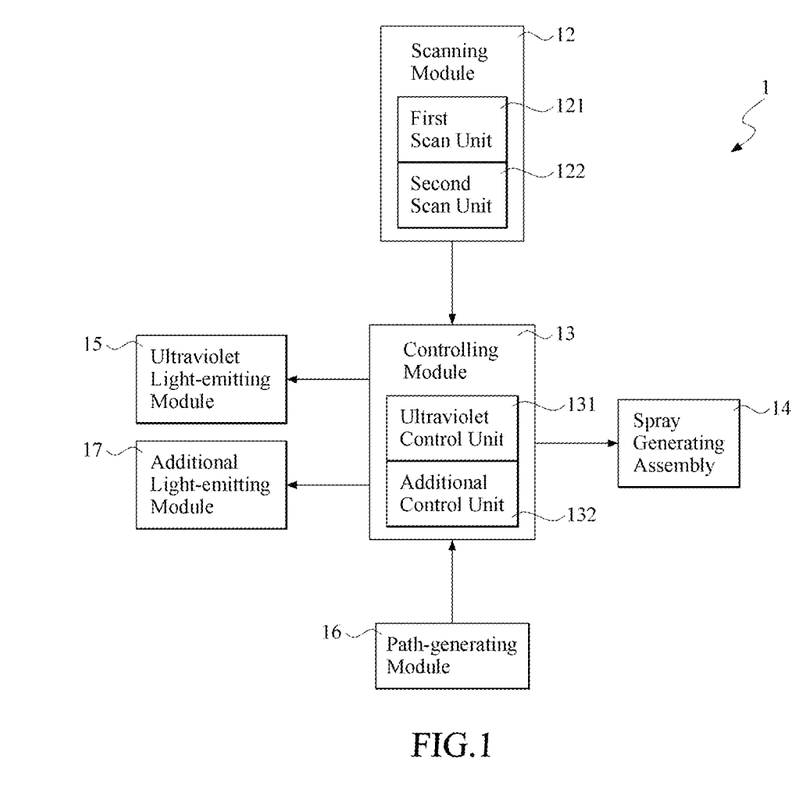
FIG. 1 is a schematic block view of a first embodiment of the mobile device for disinfecting and sterilizing with spray and ultraviolet light in accordance with this invention.
Figure 2:
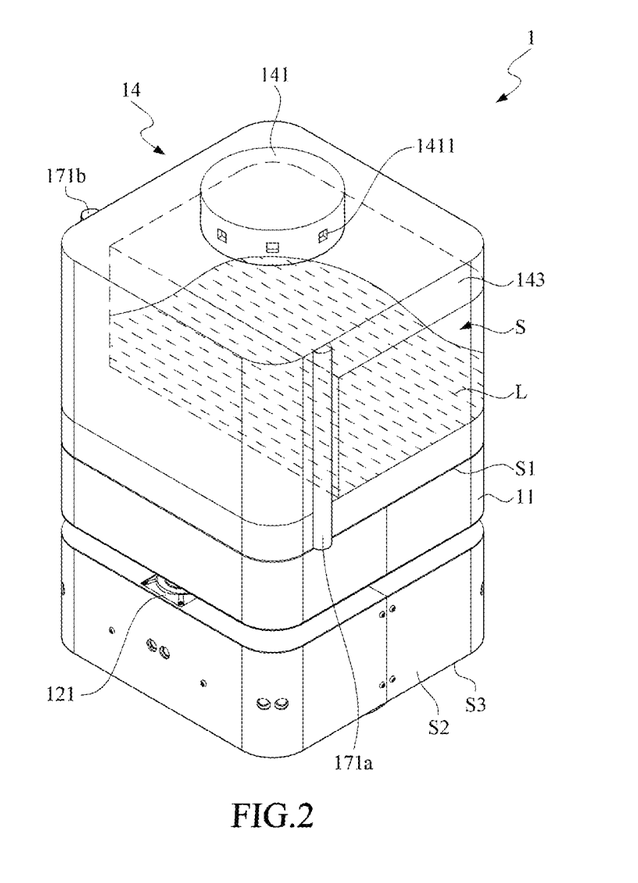
FIG. 2 is a schematic perspective view of FIG. 1.
Figure 3:
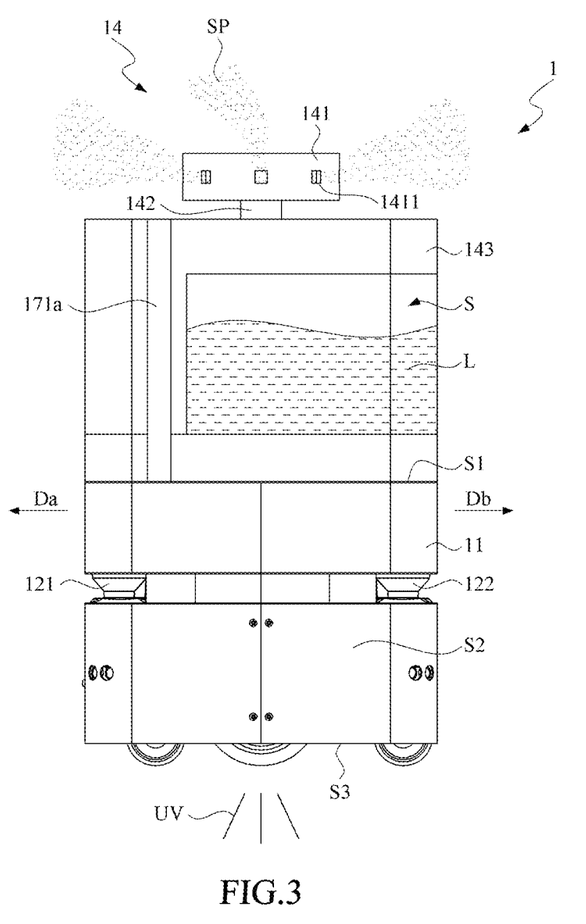
FIG. 3 is a schematic side view of FIG. 2 furnished with disinfecting and sterilizing spray.
Figure 4:
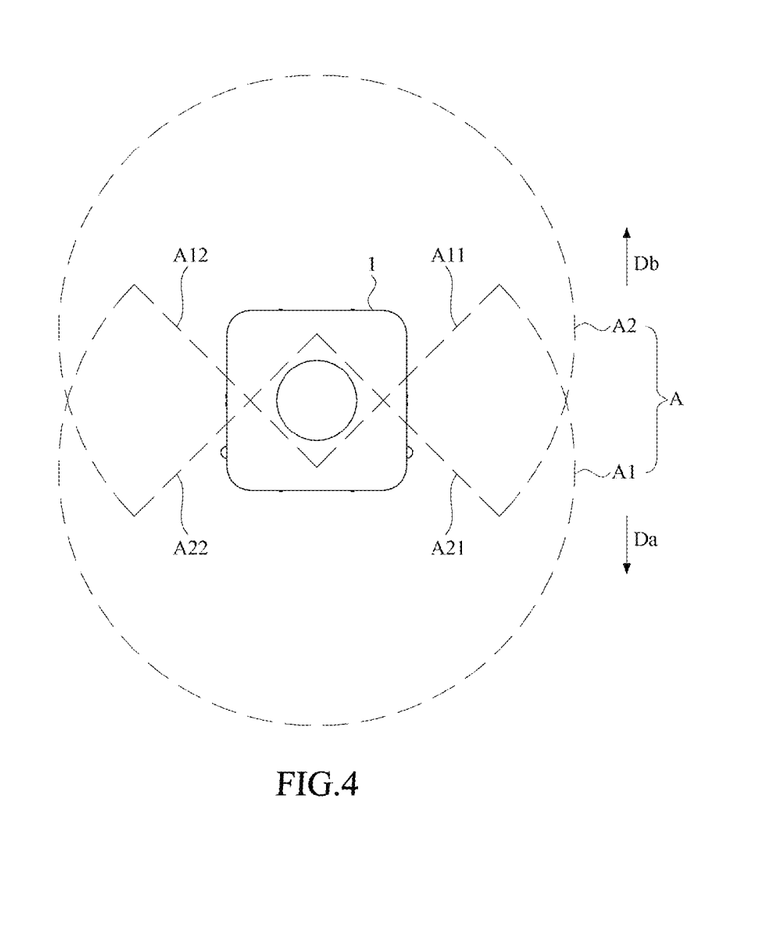
FIG. 4 is a schematic top view of FIG. 2 furnished with entire scan ranges.

Refer to FIG. 1 through FIG. 4; where FIG. 1 is a schematic block view of a first embodiment of the mobile device for disinfecting and sterilizing with spray and ultraviolet light in accordance with this invention, FIG. 2 is a schematic perspective view of FIG. 1, FIG. 3 is a schematic side view of FIG. 2 furnished with disinfecting and sterilizing spray, and FIG. 4 is a schematic top view of FIG. 2 furnished with entire scan ranges. As shown, the mobile device for disinfecting and sterilizing with spray and ultraviolet light (hereinafter being simplified as "mobile device" in the following preferred embodiment) 1 includes a mobile platform 11, a scanning module 12, a controlling module 13, a spray generating assembly 14, an ultraviolet light-emitting module 15, a path-generating module 16 and an additional light-emitting module 17.

The spray generating assembly 14, disposed on an external exposed surface of the mobile platform 11, is used for generating a disinfecting and sterilizing spray SP. In this embodiment, the external exposed surface can be, but not limited to, a top surface S1. The external exposed surface, directed to an exposed surface of the mobile platform 11, includes a top surface S1 or a lateral surface S2.

In this embodiment, the spray generating assembly 14 includes a spray head 141, a rotation member 142 and a main body 143. The spray head 141 is furnished with at least one spray nozzle 1411 (three shown in the figure, with only one labeled). The main body 143 has an accommodation space S for containing a disinfection liquid L, and the accommodation space S is spatially connected with the spray nozzles 1411. The disinfection liquid L is used for forming the disinfecting and sterilizing spray SP. The rotation member 142, connected with the spray head 141, is used for rotating the spray head 141. The spray nozzle 1411 is used for spraying out the disinfecting and sterilizing spray SP.

The ultraviolet light-emitting module 15, disposed on a bottom surface S3 of the mobile platform 11, is used for generating at least one ultraviolet beam UV.

The scanning module 12, disposed at the mobile platform 11, has an entire scan range A, and includes a first scan unit 121 and a second scan unit 122. The first scan unit 121, for scanning toward a first direction Da, has a first partial scan range A1 defined by two first scan boundaries A11, A12. The second scan unit 122, for scanning toward a second direction Db, has a second partial scan range A2 defined by two second scan boundaries A21, A22. In this embodiment, the first direction Da and the second direction Db are reverse directions.

In this embodiment, the first scan unit 121 and the second scan unit 122 of the scanning module 12 are disposed in front and rear sides of the mobile platform 11, respectively, and can (but not limited to) be fitted into the mobile platform 11. The scanning module 12 can be disposed to some other positions at the mobile platform 11, such as the top surface S1 of the mobile platform 11, each of four corners of the mobile platform 11 and the front or rear side of the mobile platform 11 (without being fitted into the mobile platform 11).

Further, since the first scan boundaries A11, A12 are extended within the second partial scan range A2 while the second scan boundaries A21, A22 are within the first partial scan range A1, thus the entire scan range A integrally formed by the first partial scan range A1 and the second partial scan range A2 would cover the surroundings of the mobile platform 11; namely, all the surroundings of the mobile device for disinfecting and sterilizing 1.

The controlling module 13 is electrically connected with the scanning module 12, the spray generating assembly 14, the ultraviolet light-emitting module 15, the path-generating module 16 and the additional light-emitting module 17.

In this embodiment, the additional light-emitting module 17 includes two additional emission units 171a, 171b disposed at the spray generating assembly 14 for generating a plurality of additional ultraviolet beams UV2. In particular, wavelengths of the ultraviolet beams UV and the additional ultraviolet beams UV2 are ranged between 260 nm and 280 nm. Practically, each of the additional emission units 171a, 171b can adopt an ultraviolet LED (UVC LED) light tube or an ultraviolet fluorescent light tube. Nevertheless, no matter what a UVC LED light tube or an ultraviolet fluorescent light tube is, each of the additional emission units 171a, 171b generally includes a Quartz glass able to transmit light and to enclose an inner tube space. In addition, the additional ultraviolet beams UV2 and the ultraviolet beams UV are radiated to different directions.

Figure 5:
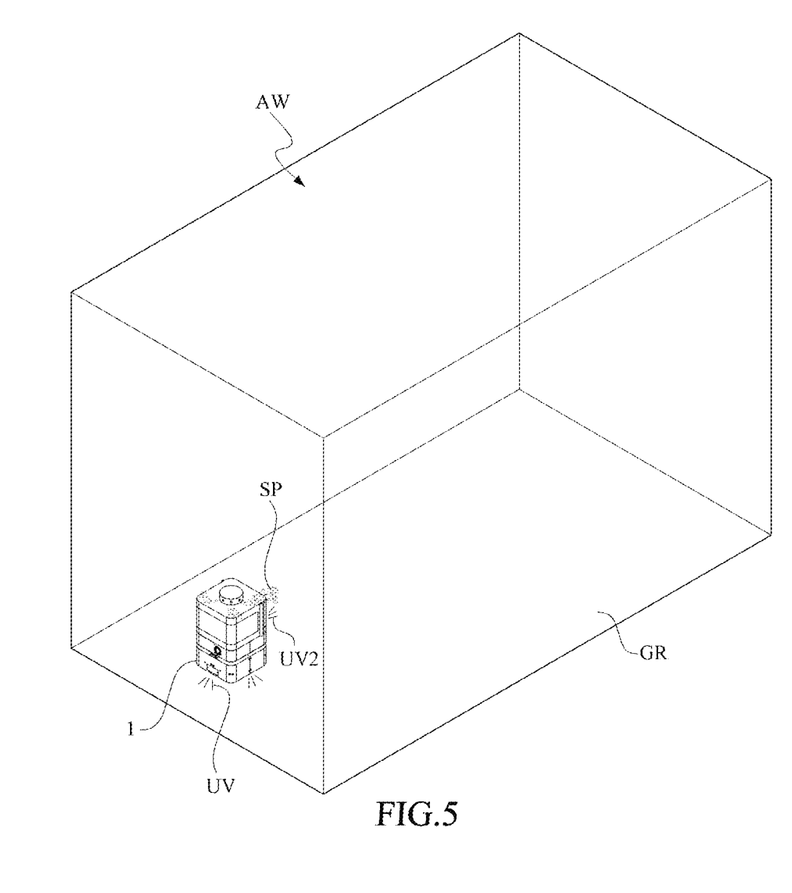
FIG. 5 is a schematic view showing that the first embodiment of the mobile device for disinfecting and sterilizing with spray and ultraviolet light provided by the present invention is performing a disinfecting and sterilizing operation.
Figure 6:
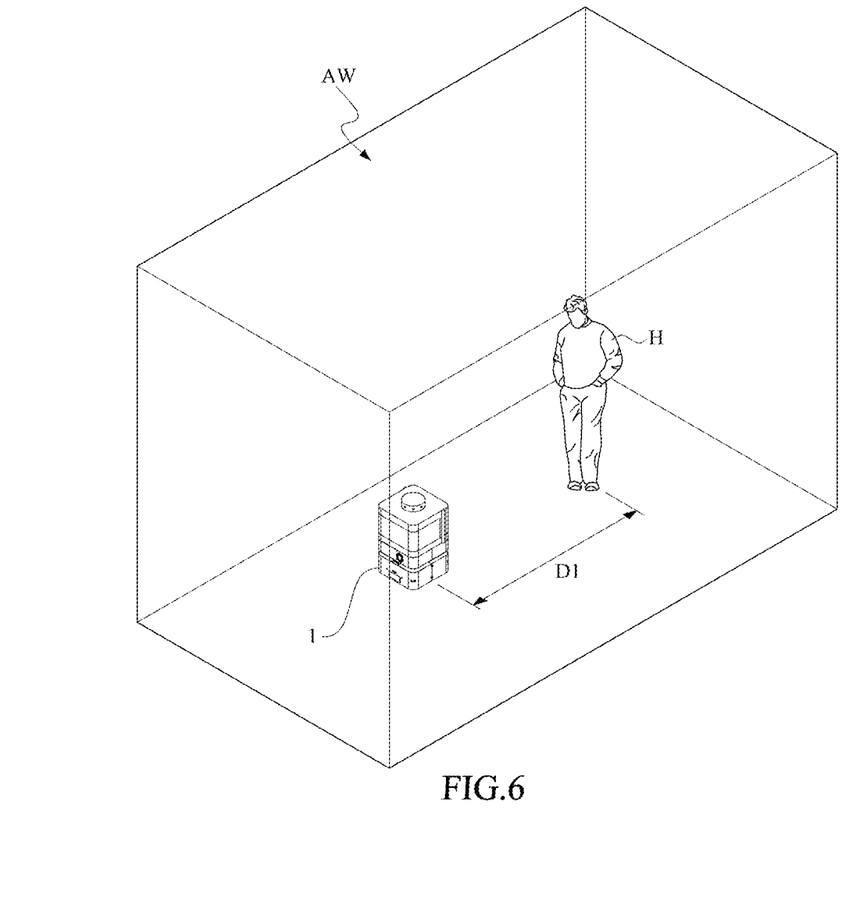
FIG. 6 demonstrates schematically that the first embodiment of the mobile device for disinfecting and sterilizing with spray and ultraviolet light provided by the present invention is scanning a human.
Figure 7:
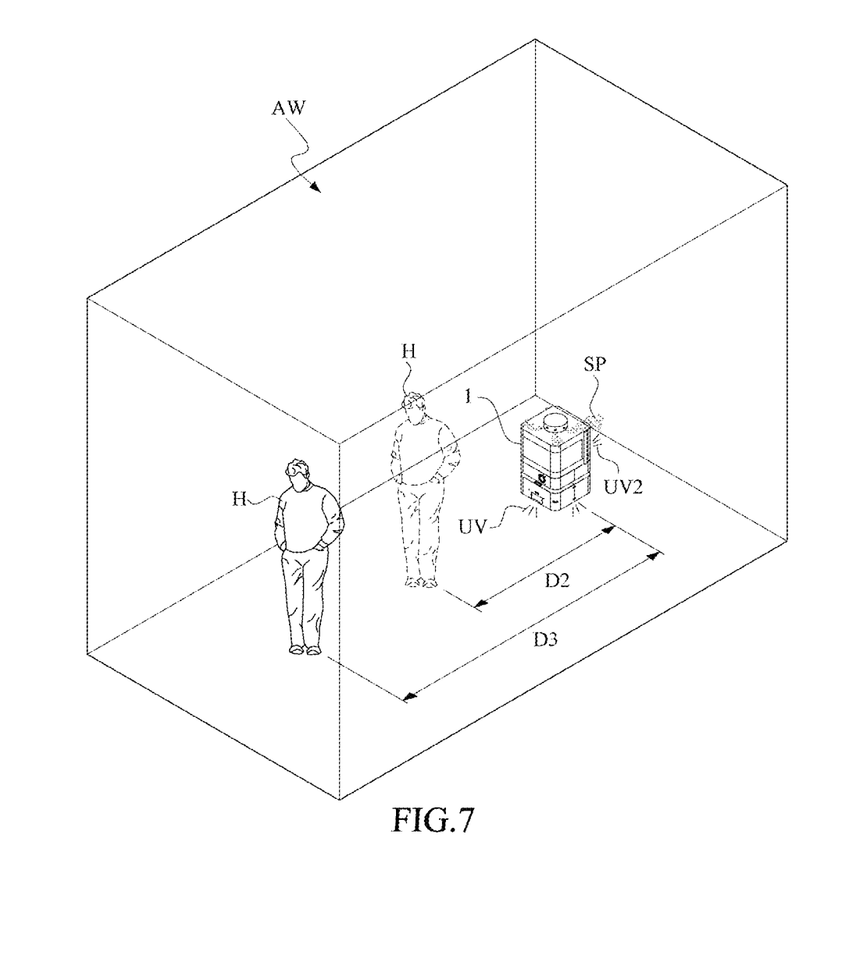
FIG. 7 shows schematically another scene that the first embodiment of the mobile device for disinfecting and sterilizing with spray and ultraviolet light provided by the present invention is scanning a human.
Figure 8:
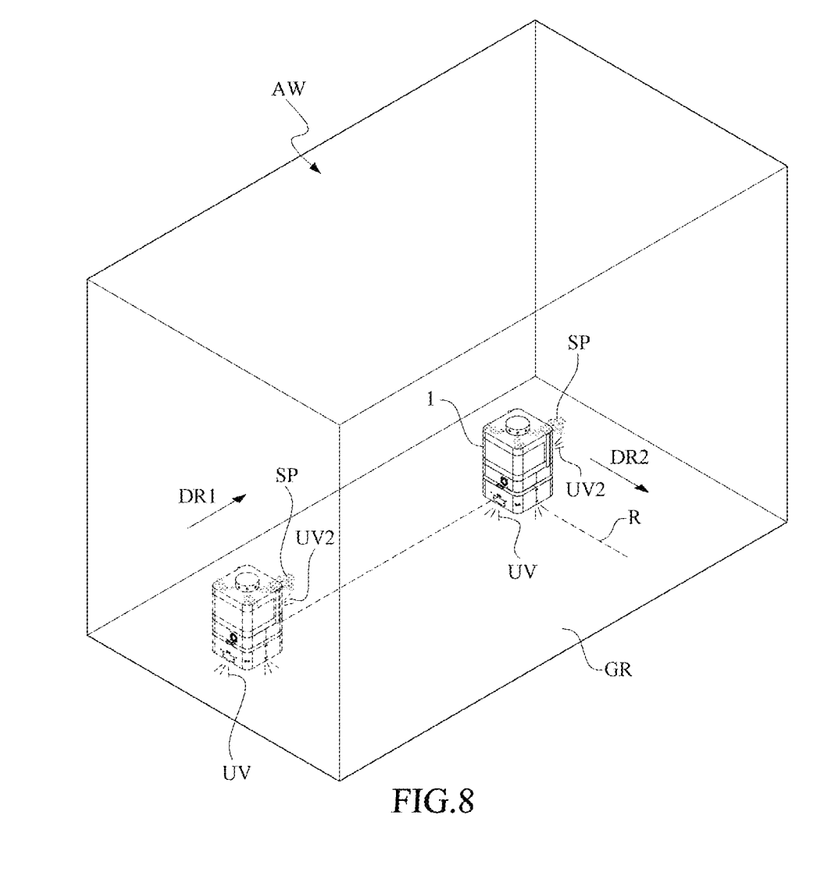
FIG. 8 demonstrates schematically that the first embodiment of the mobile device for disinfecting and sterilizing with spray and ultraviolet light provided by the present invention is in a patrol mode.
Figure 9:
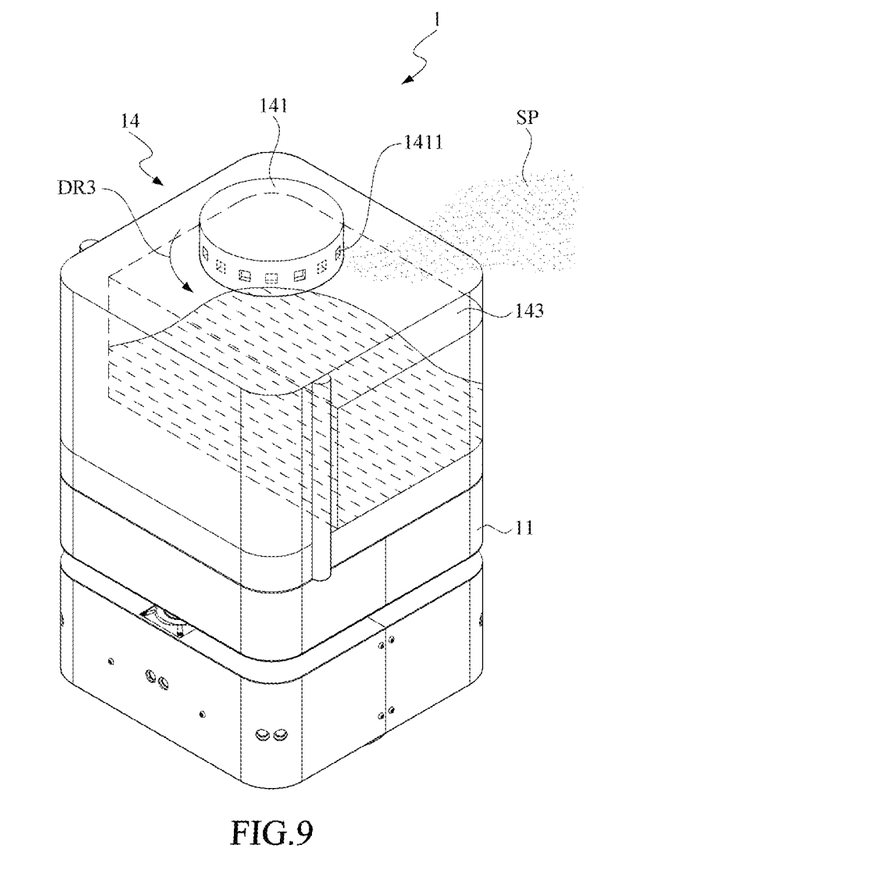
FIG. 9 demonstrates schematically that the spray head of the first embodiment of the mobile device for disinfecting and sterilizing with spray and ultraviolet light provided by the present invention is rotated by the rotation member.

Then, refer now together from FIG. 1 to FIG. 9; where FIG. 5 is a schematic view showing that the first embodiment of the mobile device for disinfecting and sterilizing with spray and ultraviolet light provided by the present invention is performing a disinfecting and sterilizing operation, FIG. 6 demonstrates schematically that the first embodiment of the mobile device for disinfecting and sterilizing with spray and ultraviolet light provided by the present invention is scanning a human, FIG. 7 shows schematically another scene that the first embodiment of the mobile device for disinfecting and sterilizing with spray and ultraviolet light provided by the present invention is scanning a human, FIG. 8 demonstrates schematically that the first embodiment of the mobile device for disinfecting and sterilizing with spray and ultraviolet light provided by the present invention is in a patrol mode, and FIG. 9 demonstrates schematically that the spray head of the first embodiment of the mobile device for disinfecting and sterilizing with spray and ultraviolet light provided by the present invention is rotated by the rotation member. As shown, the mobile device 1 can move within a working area AW to perform a spraying, disinfecting and sterilizing operation, a radiating, disinfecting and sterilizing operation and an additional radiating, disinfecting and sterilizing operation. The working area AW can be a hospital, a classroom, a building, a department store, a cafeteria, or any place that requires disinfecting and sterilizing.

The spray generating assembly 14 is used for generating the disinfecting and sterilizing spray SP to perform the disinfecting and sterilizing operation in the working area AW. The ultraviolet light-emitting module 15 is used for generating the ultraviolet beams UV to radiate a ground surface GR of the working area AW so as to perform the radiating, disinfecting and sterilizing operation onto the ground surface GR. The additional light-emitting module 17 is used for generating the additional ultraviolet beams UV2 to perform the additional radiating, disinfecting and sterilizing operation in the working area AW.

Due to physical properties, the disinfecting and sterilizing spray SP generated by the spray generating assembly 14 would go upwards. As such, the disinfecting and sterilizing spray SP may not be able to perform disinfecting and sterilizing to a lower place under the mobile device 1 or the ground surface GR of the working area AW. Thus, the ultraviolet beams UV generated by the ultraviolet light-emitting module 15 is used for radiating the ground surface GR so as to perform the radiating, disinfecting and sterilizing operation onto the ground surface GR. In addition, the additional ultraviolet beams UV2 are used for radiating the working area AW other than the ground surface GR. While the disinfecting and sterilizing sprays SP perform the spraying, disinfecting and sterilizing operation (the first disinfecting and sterilizing operation) to kill viruses and bacteria in the working area AW other than the ground surface GR, the additional ultraviolet beams UV2 perform simultaneously the additional radiating, disinfecting and sterilizing operation (the second disinfecting and sterilizing operation). Further, the ultraviolet beams UV can radiate the ground surface GR for carrying out the radiating, disinfecting and sterilizing operation (the third disinfecting and sterilizing operation). Since multiple disinfecting and sterilizing operations have been performed, thus the performance in disinfection and sterilization would be much improved.

In this embodiment, the spraying, disinfecting and sterilizing operation is one of chemical disinfecting methods, and both the radiating, disinfecting and sterilizing operation and the additional radiating, disinfecting and sterilizing operation are physical disinfecting methods. The mobile device 1 provided by this invention can perform simultaneously chemical and physical methods to disinfect and sterilize the working area AW, and thus the performance in disinfection and sterilization would be better and able to kill more wide-span viruses and bacteria.

The mobile device 1 can utilize the spray generating assembly module 14, the ultraviolet light-emitting module 15 and the additional light-emitting module 17 to perform the spraying, disinfecting and sterilizing operation, the radiating, disinfecting and sterilizing operation and the additional radiating, disinfecting and sterilizing operation over the entire working area AW, as shown in FIG. 5. Thereupon, the mobile device 1 provided by the present invention can successfully replace human labors for performing various disinfection operations, and thereby various problems caused by human work can be substantially resolved.

The disinfecting and sterilizing spray SP is at least one of the chemical compositions, including chlorine gas, two chlorine oxide, ozone, chloramine, halogen, metal ion and other ingredients. Thus, for a long inhaling time, the human would be definitely hurt. Namely, when the scanning module 12 scans and determines that a human H appears in the entire scan range A, a corresponding warning signal would be generated. As soon as the controlling module 13 receives the warning signal, the spray generating assembly 14 would be controlled to stop spraying out the disinfecting and sterilizing spray SP, so that the human H may be prevented from inhaling excessive disinfecting and sterilizing spray SP. Preferably, the controlling module 13 includes an ultraviolet control unit 131 and an additional control unit 132. Upon when the warning signal is received, the ultraviolet control unit 131 controls the ultraviolet light-emitting module 15 to stop generating the ultraviolet beams UV, such that the human H can be away from radiation of the ultraviolet beams UV. Similarly, upon when the warning signal is received, the additional control unit 132 controls the additional light-emitting module 17 to stop generating the additional ultraviolet beams UV2, such that the human H can be prevented from being radiated by the additional ultraviolet beams UV2.

Further, as shown in FIG. 6, a human H is spaced from the mobile device for disinfecting and sterilizing with spray and ultraviolet light 1 by a distance D1. When the scanning module 12 scans and determines a human H in the entire scan range A, a warning signal would be generated. Then, the controlling module 13 would turn off the spray generating assembly 14, the ultraviolet light-emitting module 15 and the additional light-emitting module 17. At the same time, the mobile 1 will not generate any disinfecting and sterilizing spray SP, any ultraviolet beam UV and any additional ultraviolet beam UV2, as shown in FIG. 6.

When the human H keeps walking to space from the mobile device 1 by a distance D3, and then if the scan of the scanning module 12 would determine that the human H has now already left the entire scan range A, the controlling module 13 would restart the spray generating assembly 14, the ultraviolet light-emitting module 15 and the additional light-emitting module 17, so as to have the spray generating assembly 14, the ultraviolet light-emitting module 15 and the additional light-emitting module 17 to resume the generation of the disinfecting and sterilizing sprays SP, the ultraviolet beams UV and the additional ultraviolet beams UV2. It shall be explained that, when the human H moves to a place behind the mobile device 1 by a distance D2 (symbolized by the dashed lines in the figure) but when the scanning module 12 scans to determine that the human H is still in the entire scan range A, then the controlling module 13 will not restart the spray generating assembly 14, the ultraviolet light-emitting module 15 and the additional light-emitting module 17.

Therefore, the 1 can prevent the human H from inhaling too much the disinfecting and sterilizing sprays SP, and also from being long-termly exposed to the ultraviolet beams UV and the additional ultraviolet beams UV, such that possible harm to the human H can be avoided.

The path-generating module 16 is used for generating a patrol route R with respect to the working area AW. The controlling module 13 would control the mobile platform 11 to move along the patrol route R, and control the spray generating assembly 14, the ultraviolet light-emitting module 15 and the additional light-emitting module 17 to generate the disinfecting and sterilizing sprays SP, the ultraviolet beams UV and the additional ultraviolet beams UV2, respectively.

As shown in FIG. 8, the controlling module 13 controls the mobile platform 11 to move along the patrol route R, firstly in a moving direction DR1 and then in a moving direction DR2. In FIG. 8, dashed lines are used to indicate previous positions of the mobile device 1. Thus, it is shown that, as the mobile device 1 moves along the patrol route R, the spray generating assembly 14, the ultraviolet light-emitting module 15 and the additional light-emitting module 17 would generate the disinfecting and sterilizing sprays SP, the ultraviolet beams UV and the additional ultraviolet beams UV2, respectively. In other words, the 1 performs the spraying, disinfecting and sterilizing operation, the radiating, disinfecting and sterilizing operation and the additional radiating, disinfecting and sterilizing operation at the same time while moving in the working area AW. The aforesaid patrol mode can be applied to a corridor, a promenade, a hall and another place with few obstacles or more space.

It shall be explained that, practically, the patrol route R is not a real path or a real surrounding road. Actually, the patrol route R is only a scheme in the working area AW, and thus plotted by dashed lines.

The controlling module 13 would control the rotation member 142 to rotate in a rotation direction DR3. Since the rotation member 142 is connected with the spray head 141, so the rotation member 142 can drive the spray head 141a to rotate in the rotation direction DR3, as shown in FIG. 9. In the figure, the dashed-lined spray nozzle 1411 stands for its previous position before rotating in the rotation direction DR3.

The spraying direction of the disinfecting and sterilizing spray SP from the spray nozzle 1411 is hard to determine, in comparison to the radiation direction of the ultraviolet beams UV and the additional ultraviolet beams UV2. Thus, in this embodiment, the controlling module 13 would control the rotation member 142 to rotate in the rotation direction DR3. Preferably, the rotation member 142 can rotate 360 degrees in the rotation direction DR3. In other words, even though the disinfecting and sterilizing spray SP sprayed out from the spray nozzle 1411 is not directional, yet a maximal disinfecting and sterilizing range can be still obtained for the rotation member 142, so as the driven spray nozzle 1411, able to perform 360-degree rotation in the rotation direction DR3 while in spraying out the disinfecting and sterilizing spray SP.

It shall be explained that the aforesaid 306-degree rotation is only one of exemplary examples of this embodiment. In some other embodiments, the rotation member 142 may be free to rotate, or limited to rotate within a range of 180, 720 or 1080 degrees.

Figure 10:
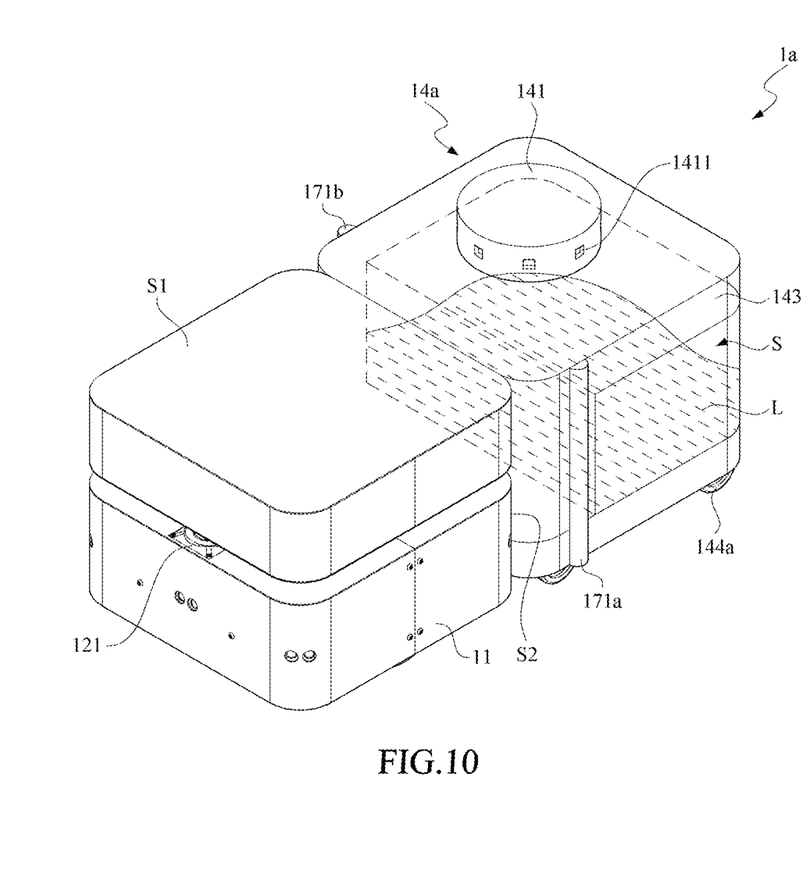
FIG. 10 is a schematic perspective view of a second embodiment of the mobile device for disinfecting and sterilizing with spray and ultraviolet light in accordance with this invention.

Finally, referring now to FIG. 10, a schematic perspective view of a second embodiment of the mobile device in accordance with this invention is shown. A difference between the 1a of this embodiment and that of the first embodiment is at the spray generating assembly 14a, and the rest of both embodiments are the same. Thus, details and descriptions for these same elements are omitted herein.

In this embodiment, the spray generating assembly 14a is disposed on the lateral surface S2 of the mobile platform 11, not the top surface S1 anymore. The spray generating assembly 14a further includes a plurality of wheels 144a (two shown in the figure with only one labeled). Since the spray generating assembly 14a is furnished with the wheels 144a, thus, when the mobile platform 11 moves, the spray generating assembly 14a can move with the mobile platform 11a via the wheels 144a.

With the spray generating assembly 14a to be disposed on the lateral surface S2 of the mobile platform 11 or behind the mobile platform 11, the corresponding use flexibility would be enhanced, and thus the height limitation upon feasible regions for disinfection and sterilization can be substantially lowered.

In summary, the mobile device for disinfecting and sterilizing with spray and ultraviolet light provided by this invention utilizes the spray generating assembly and the ultraviolet light-emitting module of the mobile platform moving within the working area to perform the spraying, disinfecting and sterilizing operation and the radiating, disinfecting and sterilizing operation. Thereupon, majority human labors can be replaced, and the risk of disease infection can be significantly reduced. Further, the spraying, disinfecting and sterilizing operation and the radiating, disinfecting and sterilizing operation are the physical disinfecting method and the chemical disinfecting method, respectively. By having two types of the disinfecting methods at the same time, the performance in disinfection and sterilization can be remarkably increased. In addition, the present invention further introduces the scanning module and the controlling module to turn off the spray generating assembly and the ultraviolet light-emitting module upon when human in the entire scan range is determined, such that the human can be prevented from being hurt by inhaling too much the disinfecting and sterilizing spray and being exposed too long to the ultraviolet beams.

While the present invention has been particularly shown and described with reference to a preferred embodiment, it will be understood by those skilled in the art that various changes in form and detail may be without departing from the spirit and scope of the present invention.

What is claimed is:

1. A mobile device for disinfecting and sterilizing with spray and ultraviolet light, used for performing a spraying, disinfecting and sterilizing operation and a radiating, disinfecting and sterilizing operation in a working area, comprising:
    a mobile platform, used for moving within the working area;
    a spray generating assembly, disposed on an external exposed surface of the mobile platform, used for generating a disinfecting and sterilizing spray for performing the spraying, disinfecting and sterilizing operation in the working area;
    an ultraviolet light-emitting module, disposed at the mobile platform, used for generating at least one ultraviolet beam to radiate a ground surface of the working area and thus to perform the radiating, disinfecting and sterilizing operation onto the ground surface;
    a scanning module, disposed at the mobile platform, defined with an entire scan range, used for generating a warning signal upon when a human within the entire scan range is determined; and
    a controlling module, electrically connected with the scanning module and the spray generating assembly, used for controlling the spray generating assembly to stop generating the disinfecting and sterilizing spray upon when the warning signal is received, so as to prevent the human from inhaling excessively the disinfecting and sterilizing spray.

2. The mobile device for disinfecting and sterilizing with spray and ultraviolet light of claim 1, wherein the spray generating assembly is disposed on a top surface of the external exposed surface of the mobile platform.

3. The mobile device for disinfecting and sterilizing with spray and ultraviolet light of claim 1, wherein the spray generating assembly includes a spray head furnished with at least one spray nozzle for spraying out the disinfecting and sterilizing spray.

4. The mobile device for disinfecting and sterilizing with spray and ultraviolet light of claim 3, wherein the spray generating assembly further includes a rotation member connected with the spray head, and is used for rotating in a rotation direction so as to have the at least one spray nozzle of the spray head to spray out the disinfecting and sterilizing spray in the rotation direction.

5. The mobile device for disinfecting and sterilizing with spray and ultraviolet light of claim 3, wherein the spray generating assembly further includes a main body having an accommodation space for containing a disinfection liquid, the accommodation space is spatially connected with the at least one spray nozzle, and the disinfection liquid is used for forming the disinfecting and sterilizing spray.

6. The mobile device for disinfecting and sterilizing with spray and ultraviolet light of claim 1, wherein the controlling module includes an ultraviolet control unit electrically connected with the ultraviolet light-emitting module and used for controlling the ultraviolet light-emitting module to stop generating the at least one ultraviolet beam upon when the warning signal is received.

7. The mobile device for disinfecting and sterilizing with spray and ultraviolet light of claim 1, wherein the scanning module includes:
    a first scan unit, scanning toward a first direction, having a first partial scan range defined by two first scan boundaries; and
    a second scan unit, scanning toward a second direction reverse to the first direction, having a second partial scan range defined by two second scan boundaries;
    wherein the two first scan boundaries are located within the second partial scan range, the two second scan boundaries are located within the first partial scan range, and the first partial scan range integrates the second partial scan range to form the entire scan range for covering surroundings of the mobile platform.

8. The mobile device for disinfecting and sterilizing with spray and ultraviolet light of claim 1, further including a path-generating module, wherein the path-generating module electrically connected with the controlling module is used for generating a patrol route with respect to the working area, and the controlling module is used for controlling the mobile platform in a patrol mode to move along the patrol route and further for controlling the spray generating assembly to generate the disinfecting and sterilizing spray.

9. The mobile device for disinfecting and sterilizing with spray and ultraviolet light of claim 1, wherein the spray generating assembly is disposed on a lateral surface of the external exposed surface of the mobile platform.

10. The mobile device for disinfecting and sterilizing with spray and ultraviolet light of claim 9, wherein the spray generating assembly includes a plurality of wheels for assisting the spray generating assembly to move with the mobile platform.

11. The mobile device for disinfecting and sterilizing with spray and ultraviolet light of claim 1, further including an additional light-emitting module disposed at the spray generating assembly for generating a plurality of additional ultraviolet beams to perform an additional disinfecting and sterilizing operation in the working area.

12. The mobile device for disinfecting and sterilizing with spray and ultraviolet light of claim 11, wherein the controlling module includes an additional control unit electrically connected with the additional light-emitting module for controlling the additional light-emitting module to stop generating the plurality of additional ultraviolet beams upon when the warning signal is received.

* * * * *